United States Patent [19]
Gardi et al.

[11] 4,256,481
[45] Mar. 17, 1981

[54] SELECTIVE HERBICIDE COMPOSITIONS

[75] Inventors: Ivan Gardi; Katalin Görög née Privitzer; Sándor Gaál; Erzsébet Dudar; Maria Kocsis née Bágyl; Márta Tasnádi all of Budapest, Hungary

[73] Assignee: Nitrokémia Ipartelepek, Füzfögyártelep, Hungary

[21] Appl. No.: 17,034

[22] Filed: Mar. 2, 1979

[51] Int. Cl.³ .................. A01N 43/86; C07D 265/04; C07D 279/04
[52] U.S. Cl. .......................................... 71/88; 71/90; 544/7; 544/54; 544/88
[58] Field of Search .................... 544/88, 7; 71/88, 90

[56] References Cited
U.S. PATENT DOCUMENTS

| | | | |
|---|---|---|---|
| 3,859,292 | 1/1975 | Dorschner et al. | 71/88 X |
| 3,881,908 | 5/1975 | Dorschner et al. | 71/88 OR |
| 3,884,671 | 5/1975 | Albright et al. | 71/88 OR |
| 4,069,036 | 1/1978 | Dorschner et al. | 71/88 OR |
| 4,124,372 | 11/1978 | Pallos et al. | 71/88 |

FOREIGN PATENT DOCUMENTS

| | | | |
|---|---|---|---|
| 2035797 | 1/1972 | Fed. Rep. of Germany | 544/88 |
| 2341810 | 2/1974 | Fed. Rep. of Germany | 71/88 |
| 2620101 | 5/1976 | Fed. Rep. of Germany | 544/88 |
| 165736 | 1/1976 | Hungary | 71/88 |
| 1454043 | 10/1976 | United Kingdom | 71/88 |
| 1457128 | 12/1976 | United Kingdom | 71/88 |
| 1457129 | 12/1976 | United Kingdom | 71/88 |
| 1457130 | 12/1976 | United Kingdom | 71/88 |
| 1484842 | 9/1977 | United Kingdom | 71/88 |

OTHER PUBLICATIONS

Hebenbrock et al., Liebigs Ann. Chem., vol. 765, pp. 78-93, (1972).
Burger, Medicinal Chemistry, 2nd Ed., Frontispage and pp. 79 to 81, Interscience Publishers, NY, (1960).

*Primary Examiner*—John D. Randolph
*Attorney, Agent, or Firm*—Karl F. Ross

[57] ABSTRACT

A selective herbicide composition comprising as an active ingredient at least one herbicidal compound selected from the group of thiolcarbamate, triazine, chloroacetanilide, carbamide or phenoxyacetic acid herbicides in admixture with a quantity of 0.1 to 50% (by weight of the herbicidal compound) of a dichloroacetamide derivative of the formula I $$\begin{array}{c} CH_2 \overset{(CH_2)_n}{\diagdown} CH_2 \\ | \qquad\qquad | \\ X \qquad\qquad N-C-CHCl_2 \\ \diagdown \underset{R_1}{C} \diagup \underset{R_2}{\phantom{C}} \quad \overset{\|}{O} \end{array}$$

wherein
X is oxygen, sulphur, SO or SO₂,
n is 0 or 1, and
R₁ and R₂ are identical or different and represent hydrogen, alkyl or halophenyl, hydroxyl or nitro; or
R₁ and R₂ together form a butylene, pentylene or hexylene group which can be substituted with one or two methyl groups, provided that if n=0, R₁ and R₂ are not for hydrogen, alkyl or substituted phenyl.

27 Claims, No Drawings

SELECTIVE HERBICIDE COMPOSITIONS

The present invention relates to selective herbicide compositions. More particularly, this invention concerns herbicide compositions which contain at least one herbicidal compound preferably selected from the following group: thiolcarbamate, triazine, chloracetanilide, carbamide or phenoxyacetic acid herbicides in admixture with 0.1 to 50%, (by weight of the herbicidal compound) of a dichloroacetamide derivative of the formula I

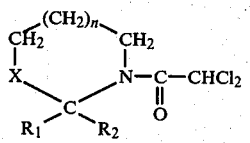

wherein
X is oxygen, sulphur, SO or $SO_2$,
n is 0 or 1, and
$R_1$ and $R_2$ are identical or different and represent hydrogen, alkyl or phenyl, substituted with halogen, hydroxyl or nitro; or
$R_1$ and $R^2$ together form a butylene, pentylene or hexylene group which can be substituted with one or two methyl groups,
provided that when n=0, $R_1$ and $R_2$ are not hydrogen, alkyl or substituted phenyl.

The above compositions have reduced phytotoxicity against cultivated plants, and are therefore suitable for the protection thereof against undesired weeds. A process for the use of said compositions for the above-mentioned purpose is also within the scope of this invention.

It is well known to those skilled in the art that, in substantial part, known herbicides are harmful to cultivated plants to be protected. The extent of this undesired phytotoxic effect is strongly dependent on the dose employed and on the conditions of application, for instance on the weather and soil conditions. Other herbicides are selective when used in small doses, but in a dose required for effective weed killing show a reduced selectivity, and become detrimental to the desired plant growth.

In the U.S. Pat. No. 3,131,509 the use of 1,8-naphthalic acid and derivatives, such as the anhydride, esters, amides thereof, is suggested to decrease the phytotoxicity of various herbicides.

According to the teaching of the Hungarian Pat. No. 165,736 the phytotoxicity of herbicide compounds can be reduced by adding an N,N-disubstituted dichloroacetamide derivative in an amount of 0.0001 to 30% by weight of the herbicide.

Most of the compounds widely used as antidotes belong to one of the above two classes of compounds; they are not, however, a final solution for this rather complicated problem. The herbicidal compounds whose phytotoxicity is to be decreased are chemically very different, and consequently possess different kind of phytotoxic activities. It is also obvious that different cultivated plants have different reactions when treated with various herbicides, and therefore the field of application of the known herbicides is strictly limited.

The object of the invention is to provide compounds of a new, class capable of decreasing the phytotoxicity of certain herbicides, and which are favorable with respect to environmental protection. The new compounds facilitate economical application of known herbicides.

It has been found that the dichloroacetamide derivatives of the formula I are capable of decreasing the phytotoxicity of herbicides of the triazine, carbamide, dichloro-acetanilide and phenoxyacetic acid type. More particularly, it has been found that when a compound of the formula I is admixed with at least one of the above-listed herbicides, in an amount of 0.1 to 50% by weight of the herbicide, the herbicidal formulations containing the mixture obtained are practically harmless to the cultivated plants and at the same time, preserve their herbicidal activity. According to another aspect of this invention the same effect can be achieved when, before sowing, the seeds of cultivated plants are admixed with a compound of the formula I (dressing), and after sowing weed-killing is performed with a known herbicide belonging to one of the above classes of compounds.

New compounds of the formula I according to the invention are illustrated in the following Table I.

TABLE 1

(Formula I)

| Compound No. | X | n | $R_1$ | $R_2$ | compound | physical const. (melting point °C., refractive index) |
|---|---|---|---|---|---|---|
| 1 | O | 0 | | pentylene | N-dichloroacetyl-1-oxa-4-azaspiro[4,5]decane | 105.5–107 |
| 2 | O | 0 | | 1'-methylpentylene | N-dichloroacetyl-10-methyl-1-oxa-4-azaspiro[4,5]decane | 100–102 |
| 3 | O | 0 | | 3'-methylpentylene | N-dichloroacetyl-8-methyl-1-oxa-4-azaspiro[4,5]decane | 119–120 |
| 4 | O | 0 | | 1,5'-dimethyl-pentylene | N-dichloroacetyl-6,10-dimethyl-1-oxa-azaspiro[4,5]-decane | $n_D^{26}$:1.5217 |
| 5 | O | 0 | | butylene | N-dichloroacetyl-1-oxa-4-azaspiro[4,4]nonane | 79–80 |
| 6 | O | 0 | | hexylene | N-dichloroacetyl-1-oxa-4-azaspiro[4,6]undecane | 81–82 |
| 7 | S | 0 | | pentylene | N-dichloroacetyl-1-thia-4-azaspiro[4,5]decane | 149–151 |
| 8 | S | 0 | | 1'-methylpentylene | N-dichloroacetyl-10-methyl-1-thia-4-azaspiro[4,5]decane | 106–109 |
| 9 | S | 0 | | 3'-methylpentylene | N-dichloroacetyl-8-methyl-1-thia-4-azaspiro[4,5]decane | 127–129 |
| 10 | S | 0 | | butylene | N-dichloroacetyl-1-thia-4-azaspiro[4,4]nonane | 83–85 |
| 11 | S | 0 | | hexylene | N-dichloroacetyl-1-thia-4-azaspiro[4,6]undecane | 96–99 |
| 12 | SO | 0 | | pentylene | N-dichloroacetyl-1-thia-4-azaspiro[4,5]decan-1-oxide | 188 |
| 13 | $SO_2$ | 0 | | pentylene | N-dichloroacetyl-1-thia-4-azaspiro[4,5]decan-1,1-dioxide | 180–181 |
| 14 | O | 1 | H | H | N-dichloroacetyl-tetrahydro-1,3(2H)-oxazine | $n_D^{26}$:1.5168 |
| 15 | O | 1 | $CH_3$ | $CH_3$ | N-dichloroacetyl-2,2-dimethyl-tetrahydro-1,3(2H)-oxazine | $n_D^{26}$:1.507 |
| 16 | O | 1 | $CH_3$ | $C_2H_5$ | N-dichloroacetyl-2-methyl-2-ethyl-tetrahydro-1,3(2H)-oxazine | $n_D^{26}$:1.4919 |
| 17 | O | 1 | | pentylene | N-dichloroacetyl-1-oxa-5-azaspiro[5,5]undecane | 111–112 |
| 18 | O | 1 | | 1'-methylpentylene | N-dichloroacetyl-11-methyl-1-oxa-5-azaspiro[5,5]undecane | 135–138 |
| 19 | O | 1 | | 3'methylpentylene | N-dichloroacetyl-9-methyl-1-oxa-5-azaspiro[5,5]undecane | 115–118 |

TABLE 1-continued (Formula I)

| Compound No. | X | n | R$_1$ | R$_2$ compound | physical const. (melting point °C., refractive index) |
|---|---|---|---|---|---|
| 20 | O | 1 | butylene | N-dichloroacetyl-1-oxa-5-azaspiro[5,4]decane | 62–64 |
| 21 | O | 1 | hexylene | N-dichloroacetyl-1-oxa-5-azaspiro[5,6]dodecane | $n_D^{26}$:1.5012 |

From Table I it can be clearly seen that most of the new compounds are in a solid, crystalline state under normal conditions and only some of them are liquid at room temperature.

Chemically compounds of the formula I belong to the broad type of acid amides and can be prepared by various methods known in the art.

According to the principles of a well-known process, compounds of the formula I can be prepared by acrylating a cyclic amine or a salt thereof with dichloroacetyl chloride, in an inert solvent, in the presence of an acid binding agent [see German Patent Specifications Nos. 2,350,547 and 2,350,800; W. R. Vanghan et al., J. Org. Chem. 26, 145 to 148 (1961)]. The inert solvent can be a ketone, such as acetone, methylethyl ketone; an aliphatic hydrocarbon, such as hexane; an aromatic hydrocarbon, such as benzene, toluene, xylene; chlorobenzene; nitrobenzene; diethylether, dimethyl sulphoxide; or chlorinated aliphatic hydrocarbons, such as methylene chloride or carbon tetrachloride. Acylation, however, takes place also in the absence of an inert solvent. Suitable acid binding agents are: organic bases, such as triethyl amine, trimethyl amine, pyridine, N,N-dimethylaniline, but in organic bases such as alkali metal carbonates, alkali metal hydrocarbonates, alkali hydroxides and aqueous solutions thereof can also be used. The acylation is generally performed at a temperature between −50° C. and 160° C., preferably between −20° C. and 40° C.

Amines used as starting compounds are five-or six-membered heterocyclic compounds, which contain one nitrogen and one oxygen or sulphuric atom and the preparation thereof is described in a large number of publications, such as J. Am. Chem. Soc. 75, 358 to 361 (1953); J. D. Doughty et al.: J. Am. Chem. Soc. 72, 2366–2367 (1950); W. H. Watanabe: J. Am. Chem. Soc. 79, 2833–2836 (1957). Both five- and six-membered amines can be prepared by reacting a corresponding hydroxyalkylamine or mercaptoalkylamine or a hydrochloride thereof with an appropriate carbonyl compound, in a solvent or without any solvent, optionally in the presence of a catalyst, at room temperature or at an elevated temperature, optionally continuously eliminating the water formed.

The catalyst can be a basic catalyst, such as an alkali metal carbonate or an acid catalysts such as hydrogen chloride, hydrogen bromide or p-toluene-sulphonic acid. Suitable solvents are various aliphatic hydrocarbons, e.g. hexane, petroleum ether; halogenated derivatives thereof. e.g. methylene chloride, carbon tetrachloride; aromatic hydrocarbons, e.g. benzene, toluene, xylene; or derivatives thereof, e.g. chlorobenzene, nitrobenzene, as well as ethers or an excess amount of the carbonyl compound taking part in the reaction.

The reaction is accomplished at a temperature of 20° C. to 200° C. By using this reaction five-membered cyclic amines are obtained by reacting aziridine with a corresponding carbonyl compound, optionally in the presence of hydrogen sulphide.

In another method, compounds of the formula I are prepared starting from an N-dichloro-acetylated hydroxyalkylamine or mercaptoalkylamine, or the hydrochlorides thereof and a corresponding carbonyl compound under the above-described reaction conditions.

In a third method an N-nitrozo derivative of the corresponding heterocyclic amines is reacted with dichloroacetyl chloride [see German Patent Specification No. 2,035,796; K. L. Hebenbrock et al., Justus Liebig, Ann. Chem. 765, 78 to 95 (1972)].

N-acylated heterocyclic amides can also be obtained by reacting a Schiff base, prepared from a corresponding aminoalcohol and a carbonyl compound, with dichloroacetyl chloride, under the reaction conditions described above [M. Businolli: Il Farmaco (Pavia) Ed. Sci. 10, 127 to 134 (1955)].

The preparation of the compounds of the formula I and their antidote activity is further illustrated in the following non-limiting Examples.

EXAMPLE 1

Preparation of N-dichloroacetyl-1-oxa-4-azaspiro[4,5]decane (compound 1)

From a boiling mixture of 64 g. (0.645 moles) of cyclohexanone and 30 g. (0.491 moles) of ethanolamine in 100 ml. of benzene the water formed is continuously distilled off. Boiling is continued until 8.8 ml. of water are separated. The reaction mixture is then cooled, 55 g. (0.55 moles) of a 40% aqueous sodium hydroxide solution are added followed by dropwise addition of 74 g. (0.5 moles) of dichloroacetyl chloride with external salt/ice cooling. The mixture is stirred for two additional hours at room temperature and thereafter washed with an aqueous hydrochloric acid solution and subsequently with water. From the neutral mixture obtained benzene is distilled off in vacuo. 10 g. (0.4 moles) of a greenish-white crystalline substance are obtained. Recrystallization from absolute ethanol affords a white crystalline product melting at 105.5° to 107° C. The structure of the named compound can be verified by IR spectrum analysis.

Analysis: Calculated: C 47.63%; N 5.50%; Cl 28.12%; Found: C 47.12%; N 5.70%; Cl 28.56%.

EXAMPLE 2

Preparation of N-dichloroacetyl-1-thia-4-azaspiro[4,5]decane (compound 7)

From a boiling mixture of 9.8 g. (0.1 moles) of cyclohexanone and 7.7 g. (0.1 moles) of 2-mercaptoethylamine in 100 ml. of benzene the water formed is continuously distilled off. Boiling is continued until 1.8 ml. of water are separated. The reaction mixture is then cooled and 11 g. of a 40% aqueous sodium hydroxide solution are added followed by dropwise addition of 14.7 g. (0.1 moles) of dichloroacetyl chloride, with external salt/ice cooling. Mixture is stirred for a further two hours at room temperature and washed with aqueous hydrochloric acid solution and subsequently with water. From the neutral mixture obtained benzene is distilled off in vacuo to give 17.2 g. (0.064 moles) of a white powder. Recrystallization from absolute ethanol yields a white crystalline product melting at 149° to 151° C. The structure of the named compound can be verified by IR spectrum analysis.

Analysis: Calculated: C 44.77%; N 5.22%; S 11.95%; Cl 26.43%; Found: C 44.51%; N 5.31%; S 12.15%; Cl 26.29%.

EXAMPLE 3

Preparation of N-dichloroacetyl-8-methyl-1-oxa-4-azaspiro[4,5]decane (compound 3)

From a boiling mixture of 11.2 g. (0.1 moles) of 4-methyl-cyclohexanone and 6.1 g. (0.1 moles) of ethanolamine in 100 ml. of benzene the formed water is continuously distilled off. Boiling is continued until 1.8 ml. of water are separated. The reaction mixture is then cooled and 8 g. (0.1 moles) of pyridine are added followed by dropwise addition of 14.7 g. (0.1 moles) of dichloroacetyl chloride with external salt/ice cooling. Further following the procedure described in Example 2, 20.7 g. (0.078 moles) of a rose, oily product are obtained. Recrystallization from absolute ethanol affords a white, crystalline product melting at 119° to 120° C. The structure of the compound obtained can be verified by IR spectrum analysis.

Analysis: Calculated: C 49.63%; N 5.26%; Cl 26.64%; Found: C 49.45%; N 5.35%; Cl 26.92%.

EXAMPLE 4

Preparation of N-dichloroacetyl-1-oxa-5-azaspiro[5,5]undecane (compound 19)

From a boiling mixture of 17.6 g. (0.18 moles) of cyclohexanone and 11.2 g. (0.15 moles) of 3-aminopropanol in 50 ml. of benzene the water formed is continuously distilled off. Boiling is continued until 2.7 ml. of water are separated. The reaction mixture is then cooled and 16 ml. (0.165 moles) of a 40% aqueous sodium hydroxide solution are added followed by a subsequent dropwise addition of 22.1 g. (0.15 moles) of dichloroacetyl chloride, with external salt/ice cooling.

Further following the procedure described in Example 2 15.7 g. (0.059 moles) of a greenish white crystalline product are obtained. Recrystallization from absolute ethanol affords a white crystalline substance melting at 111° to 112° C. The structure of the compound obtained can be verified by IR spectrum analysis.

Analysis: Calculated: C 49.63%; N 5.26%; Cl 26.64%; Found: C 49.52%; N 5.32%; Cl 26.45%.

EXAMPLE 5

Preparation of N-dichloroacetyl-1-thia-4-azaspiro[4,4]nonane (compound 10)

From a boiling mixture of 8.4 g. (0.1 moles) of cyclopentanone and 7.7 g. (0.1 mole) of 2-mercaptoethylamine in 100 ml. of benzene the water formed is continuously distilled off. Boiling is continued until 1.8 ml. of water are separated. The reaction mixture is then cooled and 8 g. (0.1 moles) of pyridine are added followed by a dropwise addition of 14.7 g. (0.1 moles) of dichloroacetyl chloride, with external salt/ice cooling.

Furtheron following the procedure described in Example 2 21.6 g. (0.085 moles) of a yellowish oily product are obtained. Recrystallization from n-hexane affords a white, crystalline product melting at 83° to 85° C. The structure of the compound obtained can be verified by IR spectrum analysis.

Analysis: Calculated: C 42.53%; N 5.51%; S 12.61%; Cl 27.89%; Found: C 42.35%; N 5.45%; S 12.80%; Cl 27.56%.

EXAMPLE 6

Preparation of N-dichloroacetyl-1-thia-4-azaspiro[4,5]decane-1-oxide (compound 12)

13.41 g. (0.05 moles) of N-dichloroacetyl-1-thia-4-azaspiro[4,5]decane are dissolved in 100 ml. of methylene chloride and to the solution obtained a solution of 9.15 g. (0.053 moles) of n-chloroperbenzoic acid in 100 ml. of methylene chloride is added dropwise, at a temperature between $-25°$ C. and $-15°$ C. The reaction mixture is then stirred at room temperature for 2 hours and subsequently cooled to 10° C. The insoluble substances are filtered off and the filtrate is washed with two 30 ml. portions of a saturated sodium carbonate solution and subsequently with water, dried over sodium sulphate and finally, evaporated to dryness.

13.23 g. of a white crystalline product are obtained, corresponding to a yield of 93%. Recrystallization from absolute ethanol affords a white, crystalline product melting at 188° C. (decomp.).

Analysis: Calculated: C 42.26%; H 5.32%; O 11.26%; N 4.93%; Cl 24.95%; S 11.28%; Found: C 42.18%; H 5.30%; O 11.35%; N 4.98%; Cl 24.90%; S 11.30%.

The structure of the compound obtained is verified by IR spectrum analysis.

EXAMPLE 7

Preparation of N-dichloroacetyl-1-thia-4-azaspiro[4,5]decane-1,1-dioxide (compound 13)

13.41 g. (0.05 moles) of N-dichloroacetyl-1-thia-4-azaspiro[4,5]decane are dissolved in 150 ml. of methylene chloride and a solution of 18.12 g. (0.105 moles) of m-chloroperbenzoic acid in 200 ml. of methylene chloride is added dropwise at a temperature of between 0° C. and 3° C. The reaction mixture is then allowed to stir at room temperature for one hour and boiled for another one hour. It is then cooled to 5° C., the precipitated solid is filtered off and washed with 50 ml. of methylene chloride. The filtrate is washed with two 50-ml. portions of a saturated sodium carbonate solution and subsequently with water, dried over anhydrous sodium sulphate and finally evaporated to dryness. 13.7 g. (91%) of a yellowish brown crystalline product are obtained, which is then recrystallized from acetone, using activated charcoal for decoloring. Melting point of the white, crystalline product obtained: 180° to 181° C. (decomp.).

Analysis: Calculated: C 40.00%; H 5.12%; O 15.99%; N 4.67%; Cl 23.66%; S 10.68%; Found: C 40.10%; H 5.08%; O 16.03%; N 4.70%; Cl 23.60%; S 10.72%.

The structure of the compound obtained can be verified by IR spectrum analysis.

All the other compounds listed in the Table I together with their physical characteristics may be prepared in an analogous way.

Some representatives of the herbicides the phytotoxicity of which is decreased by the compounds having the formula I are listed hereinbelow:

S-ethyl-N,N-dipropylthiocarbamate,
S-propyl-dipropylthiocarbamate,
S-ethyl-diisobutylthiocarbamate,
S-2,3,3-trichlorallyl-diisopropylthiocarbamate,
S-ethyl-cyclohexylethylthiocarbamate, 2-chloro-2',6'-N-(methoxymethyl)acetanilide,
9-ethylhexahydro-1H-azepine-1-carbothioate,
2-chloro-N-isopropylacetanilide,
N,N-diallyl-2-chloroacetamide,
S-4-chlorobenzyldiethylthiocarbamate,
2-chloro-4-ethylamino-6-isoproylamino-s-triazine,
2-chloro-4,6-bis-(ethylamino)-sas-triazine,
2-(4-chloro-6-ethylamino-s-triazine-2-yl-amino)-2-methylpropionitrile,
2-chloro-4-cyclopropylamino-6-isopropylamino-s-triazine,
2,4-dichlorophenoxyacetic acid,
3-(3',4'-dichlorophenyl)-1-methyl-1-(n-butyl)-urea,
2-chloro-2'-ethyl-6'-methyl-N-(1-methyl-2-methoxyethyl)-acetanilide,
2-chloro-2',6'-diethyl-N-(1,3-dioxolan-2-yl-methyl)-acetanilide,
2-chloro-2',6'-diethyl-N-(ethoxycarbonyl-methyl)-acetanilide,
2-chloro-N-ethoxymethyl-2'-methyl-6'-ethyl-acetanilide,
2-chloro-N-(2'-methoxyethyl)-2'',6''-dimethyl-acetanilide,
2-chloro-N-butoxymethyl-2',6'-diethyl-acetanilide,
2-chloro-N-(2''-methoxy-1''-methyl-ethyl)-2'-methyl-6'-ethylacetanilide,
2-chloro-N-isopropoxymethyl-2',6'-dimethylacetanilide,
N,N-hexamethylene-S-ethyl-thiolcarbamate,
N-(3-chlorophenyl)-N'-methyl-N'-methoxyurea,
N-(3,4-dichlorphenyl)-N'-methyl-N'-methoxyurea,
N-(3-chloro-4-bromophenyl)-N'-methyl-N'-methoxyurea,
2-butylamino-4-chloro-6-ethylamino-s-triazine,
2-chloro-4,6-bis-isopropylamino-s-triazine,
2-methylmercapto-4,6-bis-isopropylamino-s-triazine,
2-methylmercapto-4-ethylamino-6-tert-butylamino-s-triazine,
2-tert-butylamino-4-ethylamino-6-methoxy-1,3,5-triazine,
4-amino-6-tert-butyl-3-methylthio-4,5-dihydro-1,2,4-triazin-5-one,
2,4-dichlorophenoxyacetic acid,
2,4-dichlorophenoxypropionic acid,
B 2,4-dichlorophenoxybutyric acid,
2-methyl-4-chlorophenoxyacetic acid,
2,4,5-trichlorophenoxyacetic acid,
and the mixtures of the above compounds.

Dichloroacetamide derivatives of the formula I may be formulated alone or together with one or more of the herbicides some representatives of which have been listed hereinabove into solid or liquid compositions by means of conventional techniques widely used for the preparation of plant protecting compositions. The crystalline compounds of the formula I may for example be converted to wettable powders by the following procedure:

Wettable powder:
70.0% a compound of the formula I
17.0% kaoline
8.0% activated silica
2.5% fatty alcohol sulphonate
2.5% ligninsulphonic acid-Na By admixing the above components in the given proportions in an "Alpine" mill, a ready-for-use wettable powder composition is obtained. When also a herbicide active ingredient is employed, 50% of a herbicide and 20% of a compound of the formula I are admixed with the other ingredients.

When the compounds of the formula I are intended to be used to decrease the phytotoxicity of known herbicides prior to sowing by admixing the active ingredients with the seeds, advantageously talc is used as a carrier in an amount of 20 to B 30%.

Some of the compounds having the formula I are liquid at room temperature, and can therefore advantageously be formulated in form of emulsifiable concentrates. A typical emulsifiable concentrate consists of the following ingredients:

Emulsifiable concentrate I 20 to 50% of a compound having the formula I,
74 to 45% of a solvent (e.g. xylene),
9% polyoxyethylenealkyl ether emulgeator.

The composition of another emulsifiable concentrate is as given below:

Emulsifiable concentrate II

7% of a compound of formula I
75% of EPTC,
13% of xylene,
5% of polyoxyethylene-alkylether emulgeator.

Naturally also crystalline compounds can be formulated as emulsifiable concentrates. Emulsifiable concentrates are especially advantageous when the phytotoxicity of a liquid herbicide (e.g. EPTC) is to be decreased by means of a compound of the formula I.

Emulsifiable concentrate III 2-chloro-N-(methoxymethyl)-2',6'-diethylacetanilide—50%,
N-dichloroacetyl-1-thia-4-azaspiro[4,5]-decane—8%,
polyoxyalkylacyl emulgeator—5%
xylene—37%.

Granulate

S-propyl-N,N-diisobutylthiolcarbamate—5%,
N-dichloroacetyl-1-oxa-5-azaspiro[5,5]-undecane—0.5%,
Pumice—94.5%.

Compounds of the formula I exert their antidote activity when they are sprayed together with an inert herbicide—either formulated together or in form of a tank mixture prepared before spraying—but treatment can also be carried out before spraying the herbicide. According to an advantageous embodiment of the treatment seeds are treated with a formulation containing a compound of the formula I before sowing, and the herbicidal composition is sprayed to the soil immediately before or after sowing.

The following examples illustrate the effect of the compounds having the formula I in combination with Afalone [N-(3,4-dichlorophenyl)-N'-methyl-N'-methoxyurea], Eptam [N,N-dipropyl-S-ethylthiolcarbamate], Sencor [4-amino-5-tert-butyl-4,5-dihydro-3-methylthio-1,2,4-triazine-5-one] and Lasso [2-chloro-N-(methoxymethyl)-2',6'-diethyl-acetanilide]. For comparison 1,8-naphthalic acid anhydride and N,N-diallyl-2,2-dichloroacetamide—both known antidotes—have been used. The measure of phytotoxicity was the green weight of the plants treated. 100% was the weight of plants where were cultivated by using only mechanical weed killing.

EXAMPLE 8

The deteriorating effect of Afalone was observed in sunflower cultures. The extent of the decrease of this disadvantageous effect when compounds of the formula I were also used was also tested.

Four subsequent trials were carried out on plots of 20 m² each. Afalone 50 WP was used in a dose of 5 kg. of active ingredient/ha. Antidotes were sprayed onto the fields parallel with Afalone, in form of aqueous suspensions. The results obtained are set forth in the following Table 2.

TABLE 2

| | Dose (kg./ha.) of antidote | | |
|---|---|---|---|
| | 0.5 | 1.0 | 2.0 |
| | green weight expressed in % related to the control | | |
| Afalone | 41 | 41 | 41 |
| Afalone + 1,8-naphthalic acid anhydride | 58 | 69 | 75 |
| Afalone + N,N-diallyl-2,2-dichloroacetamide | 48 | 51 | 67 |
| Afalone + compound 2 | 78 | 92 | 95 |
| Afalone + compound 7 | 67 | 89 | 90 |
| Afalone + compound 15 | 75 | 93 | 102 |
| Afalone + compound 17 | 81 | 95 | 99 |
| Control (mechanical weed killing) | 100 | 100 | 100 |

From the measurement of the greed weight of sunflowers it can be unambiguously seen that heterocyclic dichloroacetamides according to the invention decrease the phytotoxicity of Afalone substantially better than either 1,8-naphthalic acid anhydride or N,N-diallyl-2,2-dichloroacetamide. It can also be seen that compound 17 exerts a practically 100% antidote effect.

EXAMPLE 9

In field trials substantially carried out as described in Example 8 the phytotoxicity of 5 kg./ha. of Afalone was tested on sunflower plants the seeds of which were treated with antidotes according to the invention, and known antidotes, respectively prior to sowing. Results of these trials were compared to the results obtained by mechanical weed killing (100%). It was found that smaller doses of the test compounds were sufficient to obtain the same effects as in the trials according to Example 8. The numerical results are shown in the following Table 3.

TABLE 3

| | Dose (kg./ha.) of antidote | | |
|---|---|---|---|
| | 0.25 | 0.50 | 1.00 |
| | green weight expressed in % related to the control | | |
| Afalone | 41 | 41 | 41 |
| 1,8-naphthalic acid anhydride + Afalone | 57 | 69 | 75 |
| N,N-diallyl-2,2-dichyloracetamide + Afalone | 62 | 71 | 75 |
| Afalone + compound 2 | 89 | 95 | 98 |
| Afalone + compound 7 | 78 | 86 | 90 |
| Afalone + compound 15 | 90 | 94 | 96 |
| Afalone + compound 17 | 92 | 98 | 100 |
| Control (mechanical weed killing) | 100 | 100 | 100 |

The results do not differ significantly—within the measurement's accuracy—from the results obtained in Example 1, although smaller doses of antidote were used.

EXAMPLE 10

The deteriorating effect of Eptam was observed in maize cultures. The extent of the decrease of this undesired effect when compounds according to the invention were also used was also tested.

Four subsequent field trials were carried out on fields of 20 m² each. The maized tested belonged to the hibride species "Beke 270". 13 l./ha. of Eptam 6 E liquid herbicide and various doses of antidotes were sprayed to the fields in form of a tank mixture, prior to sowing. The results obtained are set forth in the following Table 4.

TABLE 4

| | Dose (kg./ha.) of antidote | | |
|---|---|---|---|
| | 0.5 | 1.0 | 2.0 |
| | green weight expressed in % related to the control | | |
| Eptam | 48 | 48 | 48 |
| Eptam + 1,8-naphthalic acid anhydride | 60 | 64 | 70 |
| Eptam + N,N-diallyl-2,2-dichloroacetamide | 69 | 84 | 92 |
| Eptam + compound 1 | 98 | 102 | 105 |
| Eptam + compound 2 | 90 | 98 | 99 |
| Eptam + compound 3 | 94 | 97 | 100 |
| Eptam + compound 7 | 97 | 100 | 100 |
| Eptam + compound 9 | 92 | 97 | 98 |
| Eptam + compound 17 | 98 | 100 | 100 |
| Eptam + compound 19 | 96 | 98 | 102 |
| Control (mechanical weed killing) | 100 | 100 | 100 |

From the above results it is apparent that five of the seven heterocyclic dichloroacetamide tested entirely eliminated the phytotoxic effect caused by Eptam, but also the remaining two compounds exerted at least the same effect as N,N-dichloroacetamide (Ardicane) widely used for this purpose.

EXAMPLE 11

Field trials were substantially carried out as described in Example 10 with the only difference that seeds were treated with various doses of antidotes before sowing into a soil treated with 13 lit./ha. of liquid Eptam 6 E. The results obtained by measuring the green weight of plants are shown in the following Table 5.

TABLE 5

| | Dose (kg./q. seed) | | |
|---|---|---|---|
| | 0.25 | 0.50 | 1.00 |
| | green weight expressed in % related to the control | | |
| Eptam | 48 | 48 | 48 |
| 1,8-naphthalic acid anhydride + Eptam | 68 | 70 | 72 |
| N,N-diallyl-2,2-dichloroacetamide + Eptam | 69 | 75 | 80 |
| Eptam + compound 1 | 98 | 100 | 100 |
| Eptam + compound 2 | 95 | 97 | 97 |
| Eptam + compound 3 | 97 | 98 | 102 |
| Eptam + compound 7 | 98 | 102 | 105 |
| Eptam + compound 9 | 90 | 95 | 95 |
| Eptam + compound 17 | 95 | 98 | 98 |
| Eptam + compound 19 | 97 | 100 | 103 |
| Control (mechanical weed killing) | 100 | 100 | 100 |

From the results set forth in Table 5 it is apparent that although smaller doses of antidotes were employed, compounds 1, 3, 7 and 19 practically entirely eliminated the deteriorating effect of Eptam.

EXAMPLE 12

The effect of the compounds having the formula I on the phytotoxic effect of Sencor in soya bean cultures was tested. Soya plants were treated with a suspension containing 1.5 kg./hectare of Sencor and various doses of antidotes immediately after sowing. The results obtained are set forth in the following Table 6.

TABLE 6

|  | Dose (kg./ha.) of antidote | | |
|---|---|---|---|
|  | 0.5 | 1.0 | 2.0 |
|  | green weight expressed in % related to the control | | |
| Sencor | 17 | 17 | 17 |
| Sencor + 1,8-naphthalic acid anhydride | 30 | 41 | 52 |
| Sencor + N,N-diallyl-2,2-dichloroacetamide | 20 | 21 | 26 |
| Sencor + compound 1 | 42 | 65 | 72 |
| Sencor + compound 7 | 48 | 70 | 76 |
| Sencor + compound 8 | 45 | 68 | 76 |
| Sencor + compound 17 | 48 | 71 | 82 |
| Control (mechanical weed killing) | 100 | 100 | 100 |

From the above results it can clearly be seen that compounds of the formula I show a significantly better antidote effect than either 1,8-naphthalic acid anhydride or N,N-diallyl-dichloroacetamide.

EXAMPLE 13

Other trials were carried out substantially as described in Example 12 except that soya seeds were treated with antidotes and Sencor was sprayed to the soil immediately after sowing in a dose of 1.5 kg./ha.

The results obtained are set forth in the following Table 7.

TABLE 7

|  | Dose (kg./q) of seed | | |
|---|---|---|---|
|  | 0.25 | 0.50 | 1.0 |
|  | green weight expressed in % related to the control | | |
| Sencor | 17 | 17 | 17 |
| Sencor + 1,8-naphthalic acid anhydride | 51 | 64 | 70 |
| Sencor + N,N-diallyl-2,2-dichloroacetamide | 26 | 28 | 51 |
| Sencor + compound 1 | 52 | 75 | 80 |
| Sencor + compound 7 | 58 | 79 | 87 |
| Sencor + compound 8 | 55 | 75 | 82 |
| Sencor + compound 17 | 61 | 82 | 92 |
| Control (mechanical weed killing) | 100 | 100 | 100 |

The above results illustrate that on soya pre-treated with compounds of the formula I—especially with compound 17—Sencor has practically no injurious effect while 1,8-naphthalic acid anhydride and N,N-diallyl-2,2-dichloroacetamide show a much weaker antidote activity.

EXAMPLE 14

Tests were carried out to determine the phytotoxic effect of "Lasso", a composition containing 2-chloro-N-(methoxymethyl)-2',6'-diethyl-acetanilide as active ingredient in sorghum cultures and to observe how this undesired effect was influenced by adding compounds of formula I.

Four subsequent field trials were carried out on plots of 20 m² each, with 4.5 lit./ha. doses and Lasso 48 EC. Wettable powder compositions containing a compound of the formula I as an active ingredient, were suspended in water, and subsequently admixed with an aqueous emulsion of Lasso 48 EC in a quantity corresponding to the doses indicated in Table 8 below. The mixture obtained in this way was applied to the soil after sowing the sorghum, but prior to emergence (pre-emergent treatment). The results were evaluated by comparing the green weight of four weeks old plants to that of the control, which was treated by mechanical weed killing.

TABLE 8

|  | Dose (kg./ha.) of active ingredient | | |
|---|---|---|---|
|  | 0.5 | 1.0 | 2.0 |
|  | green weight expressed in % related to the control | | |
| Treatment |  |  |  |
| Lasso 48 EC | 37 | 37 | 37 |
| Lasso 48 EC + 1,8-naphthalic acid anhydride | 61 | 65 | 70 |
| Lasso 48 EC + N,N-diallyl-2,2-dichloroacetanilide | 72 | 78 | 82 |
| Lasso 48 EC + compound 1 | 95 | 97 | 102 |
| Lasso 48 EC + compound 2 | 80 | 87 | 92 |
| Lasso EC + compound 7 | 90 | 95 | 98 |
| Lasso 48 EC + compound 12 | 75 | 78 | 83 |
| Lasso 48 EC + compound 13 | 92 | 98 | 100 |
| Lasso 48 EC + compound 14 | 90 | 96 | 98 |
| Control (mechanical weed killing) | 100 | 100 | 100 |

EXAMPLE 15

Field trials were substantially carried out as described in Example 10 with the only difference that seeds were treated with various doses of antidotes of the formula I before sowing, and after sowing a 4.5 lit./ha. dose of Lasso 48 EC was applied to the fields. The results obtained by measuring the green weight of four weeks old plants and expressed in % related to the control are shown in the following Table 9.

TABLE 9

|  | Dose (kg. of active ingredient/q of seed) | | |
|---|---|---|---|
|  | 0.25 | 0.50 | 1.0 |
|  | green weight expressed in % related to the control | | |
| Treatment |  |  |  |
| Lasso 48 EC | 37 | 37 | 37 |
| Lasso 48 EC + 1,8-naphthalic acid anhydride | 68 | 71 | 73 |
| Lasso 48 EC + N,N-diallyl-2,2-dichloroacetamide | 75 | 80 | 85 |
| Lasso 48 EC + compound 1 | 98 | 105 | 110 |
| Lasso 48 EC + compound 2 | 95 | 98 | 96 |
| Lasso 48 EC + compound 7 | 97 | 102 | 105 |
| Lasso 48 EC + compound 12 | 93 | 96 | 96 |
| Lasso 48 EC + compound 13 | 94 | 98 | 107 |
| Lasso 48 EC + compound 14 | 87 | 91 | 85 |
| Control (mechanical weed killing) | 100 | 100 | 100 |

The conclusion can be drawn that the compounds of the formula I tested without exception considerably decreased or even totally eliminated phytotoxic activity of Lasso 48 EC on sorghum plants. In some instances—see for example compounds 1, 7 and 13—even a certain stimulating effect could be observed.

What we claimed is:

1. A compound of the formula:

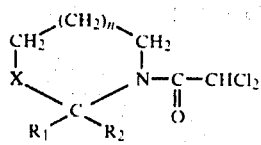

wherein
X is oxygen, sulfur, SO or SO$_2$;
n is 0 or 1; and
R$^1$ and R$^2$ together form an unsubstituted butylene, pentylene or hexylene ring, or a butylene, pentylene or hexylene ring substituted by 1 or 2 methyl groups.

2. The compound defined in claim 1 which is N-dichloroacetyl-1-oxa-5-azaspiro(5,5)undecane.

3. The compound defined in claim 1 which is N-dichloroacetyl-1-oxa-4-azaspiro(4,5)decane.

4. The compound defined in claim 1 which is N-dichloroacetyl-10-methyl-1-oxa-4-azaspiro(4,5)decane.

5. The compound defined in claim 1 which is N-dichloroacetyl-8-methyl-1-oxa-4-azaspiro(4,5)decane.

6. The compound defined in claim 1 which is N-dichloroacetyl-6,10-dimethyl-1-oxa-4-azaspiro(4,5)decane.

7. The compound defined in claim 1 which is N-dichloroacetyl-1-oxa-4-azaspiro(4,6)undecane.

8. The compound defined in claim 1 which is N-dichloroacetyl-1-thia-4-azaspiro(4,5)decane.

9. The compound defined in claim 1 which is N-dichloroacetyl-10-methyl-1-thia-4-azaspiro(4,5)decane.

10. The compound defined in claim 1 which is N-dichloroacetyl-8-methyl-1-thia-4-azaspiro(4,5)decane.

11. The compound defined in claim 1 which is N-dichloroacetyl-1-thia-4-azaspiro(4,4)nonane.

12. The compound defined in claim 1 which is N-dichloroacetyl-1-thia-4-azaspiro(4,6)undecane.

13. The compound defined in claim 1 which is N-dichloroacetyl-1-thia-4-azaspiro(4,5)decane-1-oxide.

14. The compound defined in claim 1 which is N-dichloroacetyl-1-thia-4-azaspiro(4,5)decane-1,1-dioxide.

15. The compound defined in claim 1 which is N-dichloroacetyl-11-methyl-1-oxa-5-azaspiro(5,5)undecane.

16. The compound defined in claim 1 which is N-dichloroacetyl-9-methyl-1-oxa-5-azaspiro(5,5)undecane.

17. The compound defined in claim 1 which is N-dichloroacetyl-1-oxa-5-azaspiro(5,4)decane.

18. The compound defined in claim 1 which is N-dichloroacetyl-1-oxa-5-azaspiro(5,6)dodecane.

19. The compound defined in claim 1 which is N-dichloroacetyl-1-oxa-4-azaspiro(4,4)nonane.

20. A selective herbicide composition which comprises as an active ingredient at least one herbicidal compound selected from the group which consists of thiolcarbamate, triazine, chloroacetalinide, carbamide or phenoxyacetic acid herbicides in admixture with 0.1 to 50% by weight of the herbicidal compound of a dichloroacetamide derivative of the formula:

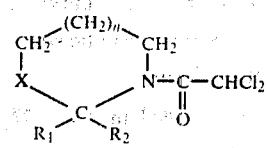

wherein
X is oxygen, sulfur, SO or SO$_2$;
n is 0 or 1; and
R$^1$ and R$^2$ together form a butylene, pentylene or hexylene ring which is unsubstituted or substituted by 1 or 2 methyl groups.

21. A selective herbicide composition as defined in claim 20 wherein the compound of the formula I, is in admixture with at least one of the following herbicide compounds: S-ethyl-N,N-dipropyl-thiolcarbamate, S-propyl-dipropylthiolcarbamate, S-ethyl-diisobutylthiolcarbamate, S-2,3,3-trichloroallyl-diisopropylthiolcarbamate, S-ethyl-cyclohexylethylthiolcarbamate, 2-chloro-2',6'-diethyl-N-(methoxymethyl)-acetanilide, 9-ethyl-hexahydro-1H-azepine-1-carbothioate, 2-chloro-N-isopropylacetanilide, N,N-diallyl-2-chloroacetamide, S-4-chloro-benzyldiethylthiolcarbamate, 2-chloro-4-ethylamino-6-isopropylamino-s-triazine, 2-chloro-4,6-bis(ethylamino)-s-triazine, 2-(4-chloro-6-ethylamino-s-triazine-2-yl-amino)-2-methylpropionitrile, 2-chloro-4-cyclopropylamino-6-isopropylamino-s-triazine, 2,4-dichlorophenoxyacetic acid, 3-(3',4'-dichlorophenyl)-1-methyl-1-(n-butyl)-carbamide, 2-chloro-2'-ethyl-6'-methyl-N-(1-methyl-2-methoxyethyl)-acetanilide, 2-chloro-2',6'-diethyl-N-(1,3-dioxolane-2-yl-methyl)-acetanilide, 2-chloro-2',6'-diethyl-N-(ethoxycarbonylmethyl)-acetanilide, 2-chloro-N-ethoxymethyl-2'-methyl-6'-ethyl-acetanilide, 2-chloro-N-(2'-methoxyethyl)-2'',6''-dimethyl-acetanilide, 2-chloro-N-butoxymethyl-2',6'-diethyl-acetanilide, 2-chloro-N-(2''-methoxy-1''-methyl-ethyl)-2'-methyl-6'-ethyl-acetanilide, 2-chloro-N-isopropoxymethyl-2',6'-dimethyl-acetanilide, N,N-hexamethylene-S-ethyl-thiolcarbamate, N-(3-chlorophenyl)-N'-methyl-N'-methoxycarbamide, N-(3,4-dichlorophenyl)-N'-methyl-N'-methoxycarbamide, N-(3-chloro-4-bromo-phenyl)-N'-methyl-N-methoxy-carbamide, 2-butylamino-4-chloro-6-ethylamino-s-triazine, 2-chloro-4,6-bis-isopropylamino-s-triazine, 2-methylmercapto-4,6-bis-isopropylamino-s-triazine, 2-methylmercapto-4-ethylamino-6-t-butylamino-s-triazine, 2-t-butylamino-4-ethylamino-6-methoxy-1,3,5-triazine, 4-amino-6-t-butyl-methylthio-4,5-dihydro-1,2,4-triazine-5-one, 2,4-dichloro-phenoxyacetic acid, 2,4-dichlorophenoxypropionic acid, 2,4-dichlorophenoxy-butyric acid, 2-methyl-4-chlorophenoxyacetic acid, and 2,4,5-trichlorophenoxyacetic acid.

22. In a process for the selective killing of undesired weeds in which a herbicidal compound is used, the improvement which comprises applying an antidotally effective amount of a compound of the formula I

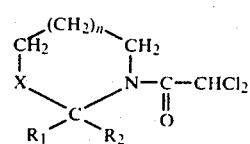
(I)

X is oxygen, sulphur atom, SO or SO$_2$
n is 0 or 1, and $R_1$ and $R_2$ together form a butylene, pentylene or hexylene group which can be substituted with one or two methyl groups.

23. The process defined in claim 22, in which the seeds of cultivated plants are treated with a composition containing a compound of the formula I prior to sowing, and the compositions contain at least one of said herbicidal compounds, as an active ingredient is applied to the soil after sowing.

24. The process defined in claim 22 wherein said compound of formula I is mixed with said herbicidal compound.

25. The process defined in claim 23 wherein the compound of formula I is applied subsequent to the application of the herbicidal compound.

26. The process defined in claim 22 wherein the compound of formula I is applied prior to the application of the herbicidal compound.

27. The process defined in claim 22 wherein the compound of formula I is applied concurrently with the application of the herbicidal compound.

* * * * *